US007001365B2

(12) United States Patent
Makkink (10) Patent No.: US 7,001,365 B2
(45) Date of Patent: Feb. 21, 2006

(54) INFUSION OF LIQUIDS INTO THE HUMAN OR ANIMAL BODY

(75) Inventor: Andrew E. Makkink, Delareyville District (ZA)

(73) Assignee: Makkinktech (PTY) Limited, Klerksdorp (ZA)

( * ) Notice: Subject to any disclaimer, the term of this patent is extended or adjusted under 35 U.S.C. 154(b) by 249 days.

(21) Appl. No.: 10/296,404

(22) PCT Filed: May 25, 2001

(86) PCT No.: PCT/ZA01/00065

§ 371 (c)(1),
(2), (4) Date: Apr. 8, 2003

(87) PCT Pub. No.: WO01/89608

PCT Pub. Date: Nov. 29, 2001

(65) Prior Publication Data

US 2003/0163112 A1    Aug. 28, 2003

(30) Foreign Application Priority Data

May 25, 2000   (ZA) ................................. 2000/2606
Aug. 31, 2000  (ZA) ................................. 2000/4569

(51) Int. Cl.
   *A61M 5/00*     (2006.01)
(52) U.S. Cl. ...................... 604/254; 604/251
(58) Field of Classification Search ............... 604/127, 604/246, 251–254, 256, 260–262
See application file for complete search history.

(56) References Cited

U.S. PATENT DOCUMENTS

| 3,738,361 | A |   | 6/1973  | Price |
|-----------|---|---|---------|-------|
| 4,038,982 | A |   | 8/1977  | Burke et al. |
| 4,269,222 | A |   | 5/1981  | Palti |
| 4,769,007 | A | * | 9/1988  | Hsu ........................... 604/127 |
| 5,360,412 | A |   | 11/1994 | Nakao et al. |
| 5,730,730 | A |   | 3/1998  | Darling, Jr. |

FOREIGN PATENT DOCUMENTS

| DE | 4319115 A1 | 12/1994 |
| DE | 19826655   | 12/1999 |

(Continued)

OTHER PUBLICATIONS

International Search Report dated Nov. 27, 2001 by th EPO/PCT.

*Primary Examiner*—Sharon Kennedy
(74) *Attorney, Agent, or Firm*—Marshall, Gerstein & Borun LLP (57) ABSTRACT

An infusion device includes an upstream pressure control device and a downstream flow control device. The device receives infusion liquid via an inlet and controls the level of liquid in a chamber by means of a float which can close both the inlet and an outlet. A filtered vent maintains atmospheric pressure in the chamber. The device receives infusion liquid at constant head via a flow pipe. A dripper delivers droplets into an airtight chamber. A taper needle renders an orifice adjustably open to a desired degree to deliver liquid at a selected rate. Screw threaded adjustment and calibration means allow calibrated adjustment. A flow pipe delivers a metered flow of infusion liquid for infusion into a human or animal body.

12 Claims, 4 Drawing Sheets

FOREIGN PATENT DOCUMENTS

| | | |
|---|---|---|
| EP | 0 284 315 A2 | 9/1988 |
| EP | 0812596 A1 | 12/1997 |
| JP | 9262289 | 10/1997 |
| RU | 2014849 C1 | 6/1994 |
| RU | 2029566 C1 | 2/1995 |
| RU | 2033811 C1 | 4/1995 |
| RU | 2054952 C1 | 2/1996 |
| RU | 2063257 C1 | 7/1996 |
| RU | 2110284 C1 | 5/1998 |
| RU | 9167 U1 | 2/1999 |

* cited by examiner

INFUSION OF LIQUIDS INTO THE HUMAN OR ANIMAL BODY

REFERENCE TO RELATED APPLICATIONS

The present application claims the benefit of priority of International Patent Application No. PCT/ZA01/00065 filed on May 25, 2001, which application claims priority of South African Patent Application No. 2000/2606 filed May 25, 2000 and South African Patent Application No. 2000/4569 filed Aug. 31, 2000. The entire text of the priority application is incorporated herein by reference in its entirety.

This invention relates to infusion of liquids into the human or animal body. It relates more specifically to a method of operating an infusion device, to a pressure control device for use with an infusion device, to a flow control device and to an infusion device.

In an infusion device known to the Applicant, also colloquially known in South Africa as a "drip", liquid to be infused is obtained from a source or reservoir. The reservoir is usually in the form of a pouch which is hung upside down and which is tapped from a port which is at the bottom of the pouch when hung. The liquid is conducted via a compressible, flexible tube of synthetic polymeric material via a metering device to an infusion needle applied to the human or animal body. The metering device includes a droplet inducer dripping the liquid in droplets into a transparent chamber to allow the droplets to be counted. The flow rate is controlled by pinching the tube in a converging device between a base and a roller which is rollingly adjusted to and fro along the base to obtain an appropriate degree of pinching.

In accordance with a first aspect of this invention, broadly, there is provided a method of operating an infusion device infusing liquid into the human or animal body, the method including establishing a constant hydraulic head of the liquid downstream of and in flow communication with a reservoir of said liquid and upstream of a flow control device, metering a predetermined flow of said liquid by means of the flow control device into a flow line, maintaining said hydraulic head constant, and infusing said predetermined flow of said liquid via said flow line into the human or animal body.

More specifically, in accordance with the first aspect, there is provided a method of operating an infusion device infusing liquid into the human or animal body, the method including maintaining a constant level of said infusion liquid in a pressure control device which is in flow communication with a reservoir of said liquid, feeding said liquid under a constant liquid head commensurate with said constant level of said infusion liquid into a flow line which flow line incorporates an adjustable flow control device and which terminates in an infusion needle infusing said liquid into the human or animal body.

The method may include subjecting said level of said liquid to atmospheric pressure via a vent hole open to atmosphere. The method may then advantageously include filtering atmospheric air passing through said vent hole to prevent contamination of said liquid. An appropriate filter for medical use may be used.

Maintaining said constant level of said infusion liquid in said pressure control device, may include arranging a float controlled valve in a chamber of said pressure control device below the reservoir and spaced above the flow control device to maintain a constant liquid level in the chamber.

The method may further include maintaining said flow line in constant orientation. It may be maintained substantially vertically.

Generally, the method may include passing the liquid in the flow control device via an orifice and appropriately adjusting the orifice to control the flow of liquid through the orifice. More specifically when the device includes a needle and seat arrangement, the orifice being provided in the seat, the method may include adjusting the relative positions of the needle and the seat to adjust an effective size of the orifice.

By way of development, the method may include sensing when the level in the level chamber has dropped to below a predetermined limit and generating a signal by means of which an alarm can be activated.

In accordance with a second aspect of this invention, there is provided a pressure control device for use with an infusion device for infusing liquid into a human or animal body, the infusion device including
 a chamber;
 an inlet into the chamber which inlet includes a connector for connecting the chamber in flow communication to a reservoir of infusion liquid;
 an outlet from the chamber which outlet includes a connector for connecting the chamber in flow communication to a flow line for conducting the infusion liquid; and
 a level control mechanism for controlling a level of said infusion liquid in the chamber at a constant level.

A vent hole may be provided at a high level through a wall of the chamber to subject said level of liquid in the chamber to atmospheric pressure. Advantageously, there may be provided a filter associated with said vent hole for filtering air passing through the vent hole.

Conveniently, said level control mechanism may include a float which is buoyant in said infusion liquid and a closure connected to the float and being aligned with said inlet into the chamber to close the inlet when the level of infusion liquid in the chamber rises above a predetermined upper limit. Said closure may be an inlet closure, the level control device including a seat in the outlet from the chamber and an outlet closure connected to the float and arranged to close the outlet against communication with the atmosphere via said vent hole when the level of infusion liquid in the chamber drops below a predetermined lower limit. This will prevent air from entering the infusion device and thus the human or animal body when the reservoir of infusion liquid runs dry. Advantageously one of said seat in the outlet and said outlet closure may be of a material which is more pliable than the other of said seat in the outlet and said outlet closure, to enhance the integrity of sealing. Preferably, the seat may be of the pliable material. The material which is the more pliable may be a silicone based polymer material.

In accordance with a third aspect of this invention, there is provided a flow control device suitable to form part of an infusion device for use in infusing a liquid into the human or animal body, which flow control device includes an orifice and an adjustable restrictor arranged, adjustably, to restrict flow through the orifice to a desired degree.

The orifice and restrictor may be in the form of a needle and seat arrangement, the needle being taper.

The flow control device may include a chamber having an inlet by means of which it is connectable in fluid flow communication to a pressure control device, an outlet connectable to a tube for connection to the animal or human body, the needle and seat arrangement being provided in the chamber and the flow control device further including a droplet inducer in the chamber and being arranged to drip liquid to allow the droplets to be counted. The droplet inducer may be arranged upstream of the orifice.

The chamber of the flow control device may include inner and outer portions which are screw threadingly, rotatably, connected to each other, the needle and the seat each being connected respectively to one of the inner and outer portions, adjustment of the needle relative to the seat being effected by relative screwing of said inner and outer portions of the chamber.

The inner and outer portions may include calibration markings to facilitate adjustment of the needle relative to the seat to a desired degree.

The inner and outer portions may be sealed against each other to render the chamber of the flow control device airtight. Sealing may be by means of an 'O' ring.

In accordance with a fourth aspect of this invention, there is provided an infusion device for use in infusing an infusion liquid into the human or animal body, the infusion device including
  a pressure control device in accordance with the second aspect of this invention;
  a flow control device in accordance with the third aspect of this invention; and
  a flow line in which said pressure control device and said flow control device are incorporated in flow communication arrangement, the flow line having a downstream end for connection to an infusion needle.

By way of development, the infusion device may include a sensor arranged to sense when the level in the level chamber drops below a predetermined level, the sensor being adapted to generate a signal for indicating a low level condition.

The invention is now described by way of examples with reference to the accompanying diagrammatic drawings.

Figure 1:
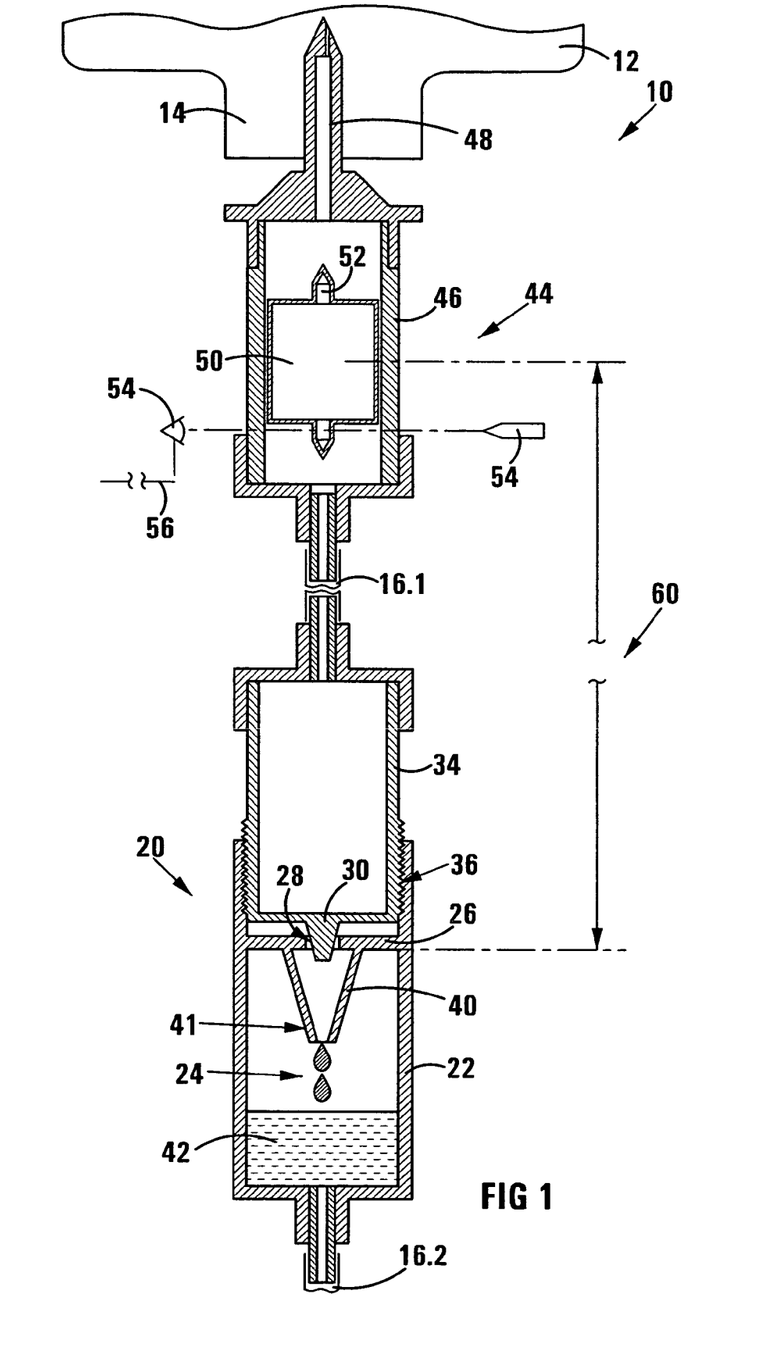
FIG. 1 shows, in sectional side view, fragmentarily, an infusion device in accordance with the invention.

With reference to FIG. 1 of the drawings, an infusion device in accordance with the invention is generally indicated by reference numeral 10. The infusion device 10 conducts a liquid to be infused from a source in the form of a pouch 12 (shown fragmentarily) at a predetermined flow rate to a patient (not shown). The infusion device 10 leads from a port 14 of the pouch 12 via a flow line 16 to the patient. The flow line 16 usually terminates in an infusion needle by means of which the liquid is administered intravenously.

The infusion device 10 includes a flow control device 20 in accordance with the invention in the flow line 16. The flow control device 20 includes a housing 22 defining a chamber 24 which is in communication with a downstream portion 16.2 of the flow line 16.

A collar 26, which is peripherally fast with the housing 22, defines an orifice or seat 28. In line with the seat 28 and immediately thereabove, there is provided a complementary needle 30 which is advantageously taper and which is secured foraminously to an upper housing 34 which is screw threadingly received as shown at 36 above the housing 22. By means of the screw threads 36, the taper needle 30 can be adjusted into and out of the seat 28 to an appropriate degree thereby to adjust the size of the orifice and thus also the flow rate through the orifice.

Below the orifice 28, and aligned therewith, there is provided a droplet inducer 40 which delivers the metered infusion liquid in the form of droplets into the chamber 24 where it accumulates as indicated at 42. The droplet inducer 40 acts as a funnel having a restricted opening 41 at a bottom. Liquid runs along taper sides thereof to exit in droplet form through the restricted opening. The droplets are counted against time to measure the actual flow rate. As the droplets remain relatively constant in volume or size, it is possible to deduce the flow rate (e.g. ml per minute) infused into the patient, from a droplet count against time.

The infusion device 10 includes a pressure or level control device in accordance with the invention, and which is generally indicated by reference numeral 44. The pressure or level control device 44 includes a housing 46 which, in this embodiment, is directly connected via an inlet 48 in the form of a needle with the interior of the pouch 12 i.e. with the liquid to be infused.

A float 50, including, at an upper end thereof, a taper closure projection 52 for progressively closing in a complemental seat, is floatingly accommodated within the housing 46. The flotation or buoyancy of the float 50 is selected to maintain inflow of liquid from the pouch 12 via the inlet 48 at a rate commensurate with flow rate through the flow control device 20 such that a constant level is maintained within the housing 46. If the flow rate into the housing 46 is too high, the float 50 is lifted and the taper closure projection 52 progressively closes into the seat to adjust the level of liquid in the housing 46 toward a neutral level. Conversely, when the level drops, the float 50 drops with it thus causing the closure projection 52 to withdraw from its seat to increase the flow to bring the level in the housing 46 back to the neutral level.

In this fashion, a substantially constant head 60 is maintained between the orifice 28 of the control device 20 and the level in the housing 46. In this way, a constant pressure gradient is maintained over the orifice 28 to render the flow through the orifice 28 constant for any specific adjustment of the needle 30.

Preferably, an upper portion of the flow line 16.1 between the pressure control device 44 and the flow control device 20 is kept at constant orientation, conveniently vertical.

By way of development, a sensor system, diagrammatically indicated by reference numeral 54, is provided in association with the float 50 to sense undue dropping of the float 50 which may indicate that attention is required, for example when the liquid in the pouch 12 has run out. The sensor 54 may, for example, be an optical sensor adapted to generate a signal when the float 50 blocks the optical path, the signal being conducted by a signal line 56 to trigger an alarm when the float 50 drops unduly.

It is frequently required to filter a liquid being infused into the human or animal body. Thus, by way of further development, the Applicant proposes to provide, if required, a mediafilter into the device, advantageously into the chamber 24. Such mediafilter may, for example, be in the form of a sock covering the orifice body from below, or in the form of a lining lying against a bottom portion of the chamber 24, which bottom portion may then be rounded, or in the form of a capsule sealing against an inner periphery of the housing 22, or the like.

It is a first advantage of the infusion device 10 that the flow rate through the flow control device 20 can be adjusted easily and accurately with fine resolution by screwing the needle 30 deeper into or shallower into the orifice 28. The Applicant believes that this is a large improvement over the existing device known to him where, as mentioned above, the flow line is compressed between a roller and a taper base. The Applicant is opinion that such prior art device is not user friendly in that it is difficult to adjust accurately. Furthermore, the integrity of the device is not good as it easily gets out of adjustment, for example due to natural resilience in the tube which is being compressed, due to being knocked by a passer by, and the like.

The Applicant regards it as a very important advantage that the hydraulic head causing the flow in the device of the invention is maintained constant. It is to be appreciated that the flow rate is a factor of the hydraulic head, and should the hydraulic head change, the flow rate would change commensurately. In this regard, in the prior art device, the Applicant has found that the level of liquid in the pouch, which determines the hydraulic head, recedes through an appreciable height from full to empty which makes an appreciable percentage difference in the hydraulic head, which directly influences the flow rate. Thus, either the flow rate changes through a substantial percentage or the change can be curtailed by frequent re-adjustment of the flow rate by means of the prior art device which, as mentioned above, is not easy to use and is not easy to adjust accurately. Thus, the prior art device requires continual monitoring and attention from medical personnel.

Thus, in those two aspects, the Applicant believes that the invention improves markedly on the prior art.

The Applicant envisages that the components of the device may, generally, be in the form of synthetic plastics mouldings, and that the device will be disposable.

The Applicant is of opinion that the use of the flow control device without the pressure or level control device on the one hand, and the use of the pressure or level control device without the specific flow control device on the other hand, would be an improvement over the prior art. Naturally, the use of both features would make a large improvement on the prior art.

As a compromise, instead of the use of the pressure or level control device, the Applicant proposes that the pouch containing the liquid be used in horizontal orientation rather than vertical orientation and that the difference in liquid level when full and the liquid level when empty would be diminished in that fashion. That, in turn, will ameliorate the change in the flow rate.

Figure 2:
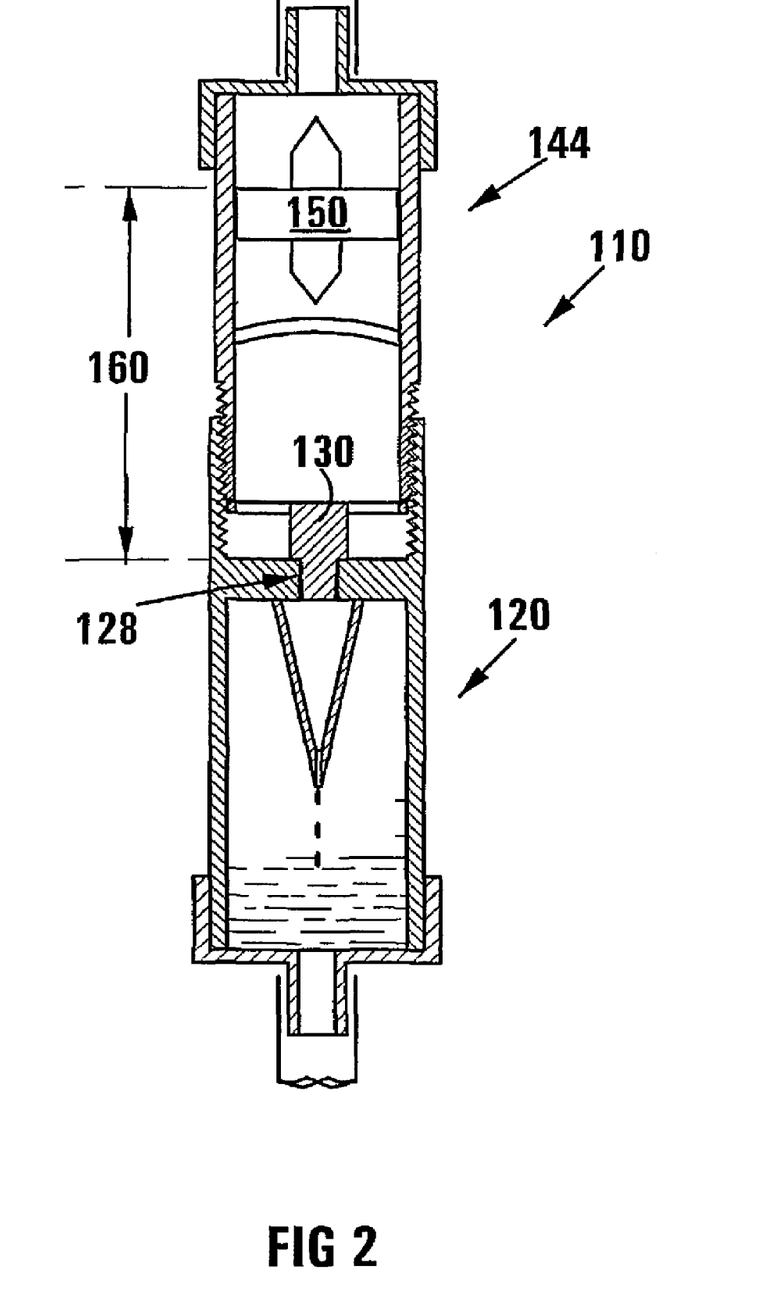
FIG. 2 shows, in sectional side view, a further embodiment of an infusion device, which is not in accordance with the invention.

With reference to FIG. 2, another embodiment of an infusion device, which, however, is not in accordance with the invention, is generally indicated by reference numeral 110. In principle, the infusion device 110 is similar to the infusion device 10 of FIG. 1 and virtually all of the features or components are similar. Thus, the embodiment 110 is not again described, but emphasis is placed merely on a single important difference, namely that the flow control device 120 and the pressure or level control device 144 are integrated in a single component. The Applicant believes that the embodiment of FIG. 2 will have a cost advantage over the embodiment of FIG. 1, and that it will also be more user friendly in so far as one component only needs to be handled. However, the Applicant is aware that, ideally, a relatively large hydraulic head is required to improve the accuracy in adjustment and to minimize fluctuations. Such a large hydraulic head can easily be obtained with the embodiment of FIG. 1, whereas, in the embodiment of FIG. 2, the hydraulic head 160 would necessarily be limited.

In other respects, it is believed that the embodiment of FIG. 2 will have the same advantages as mentioned above for the embodiment of FIG. 1.

Figure 3:
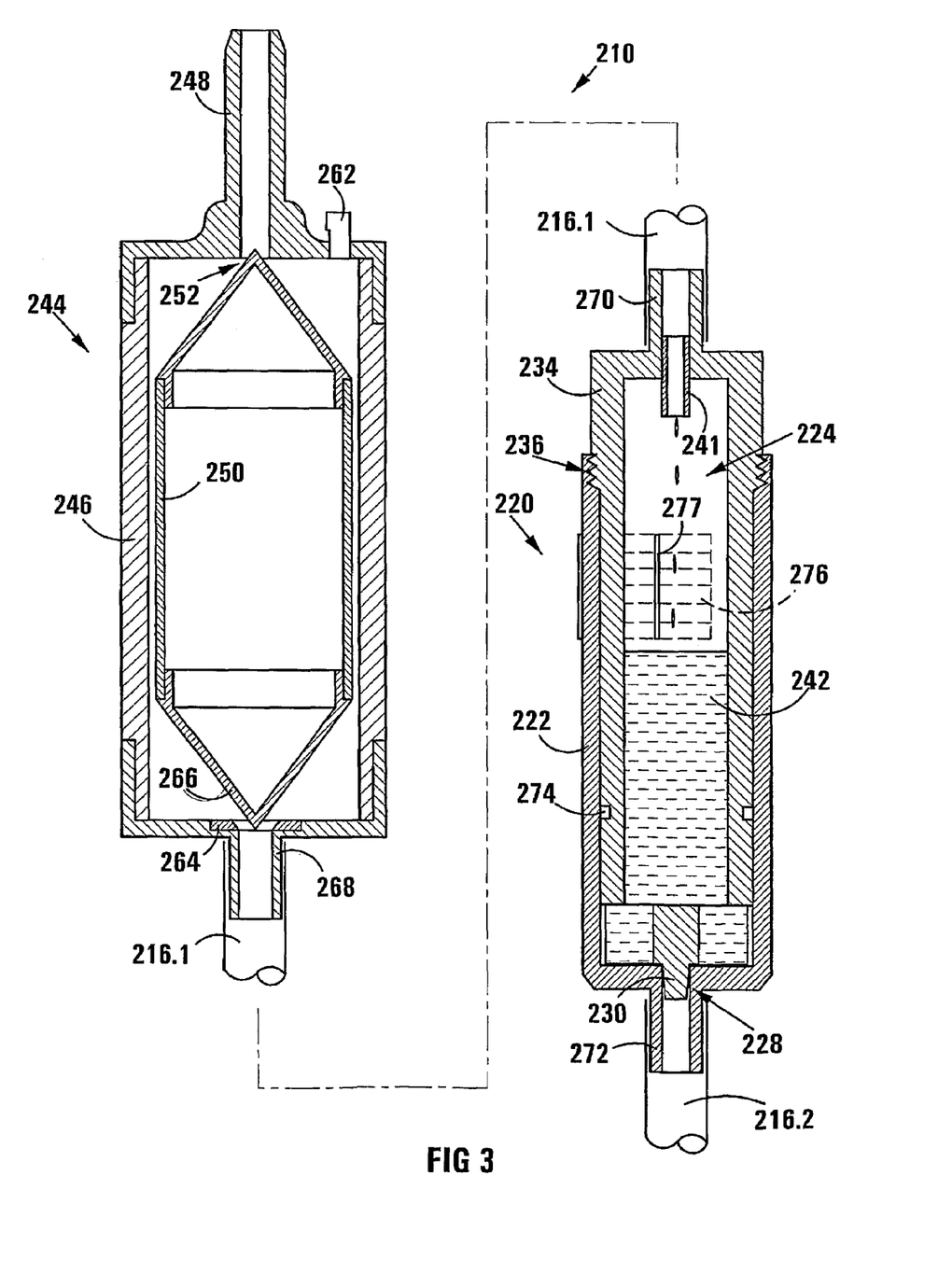
FIGS. 3 and 4 show, in sectional side views, further embodiments of an infusion device in accordance with the invention.

With reference to FIG. 3, yet a further embodiment of an infusion device in accordance with the invention is generally indicated by reference numeral 210. The infusion device 210 is similar, even identical, in many respect to the infusion device 10 of FIG. 1. Like reference numerals are generally used to indicated like features or like components. Furthermore, the device of FIG. 3 is not described in detail, but emphasis is placed on aspects in respect of which it differs from the infusion device of FIG. 1.

In the pressure or level control device 244, the housing 246 is vented to atmosphere by means of a filtered nipple 262 provided at a high level in the housing 246 i.e. at a level higher than the level to which infusion liquid is controlled within the housing 246. In this fashion, the pressure in the housing 246 above the level of infusion liquid, is maintained constant at atmospheric pressure. It is important that ambient air passing via the nipple 262 is medically effectively filtered to ensure that the infusion liquid is not contaminated.

The pressure control device 244, in its outlet 268, includes a seat 264 of pliable silicone based polymer to allow a closure 266 at a lower end of the float 250 to seat tightly in the seat 264 in the event that the level of infusion liquid in the housing 246 drops below a predetermined value. Such a condition can, for example, occur when the reservoir with infusion liquid runs dry. This feature ensures that infusion of liquid into the human or animal body is interrupted and prevents an airlock in the infusion device and thus also prevents air from being introduced into the human or animal body. It is important that the seat 264 is of a soft pliable material to enhance integrity of sealing between the closure 266 and the seat 264.

In the control device 220, the droplet inducer 241 is provided in an inlet of the flow control device, i.e. upstream of the orifice 228.

Inner and outer portions respectively 234 and 222 of the flow control device 220 are screw threadingly connected as shown at 236 to allow a taper needle 230 to move into and out of its seat 228 provided in an outlet 272 of the flow control device. This aspect has been described above with reference to FIG. 1. However, it is to be appreciated that, because of the droplet inducer 241 being above the orifice 228, there is a volume within the inner portion 234 which is air filled, i.e. not filled with infusion liquid. To maintain an effective constant hydraulic head upstream of the orifice 228, it is thus necessary that the inner and outer portions 234, 222 are sealed against each other in air tight manner. This is ensured by the provision of an "O" ring 274 intermediate the inner and outer portions 234, 222.

Conveniently, a calibration scale is provided on the device. For example, markings indicating flow rate are provided on a backing strip 276 and a pointer 277 is provided on the inner portion 234 such that the calibration markings opposite the pointer can be read for various adjustments between the inner and outer portions. Conveniently, the arrangement is such that one revolution of the portions 234 and 222 relative to each other adjusts the flow rate between zero and a maximum.

The device 220 is calibrated such that droplets need not be counted, but can be counted as a check on the calibration.

If desired, a series of clicks or notches can be provided in the adjustment mechanism such that adjustment can easily be effected in step wise fashion, from one click to the next.

The Applicant has found that the needle 230 may advantageously have a very small taper, of the order of 0,5° or 1° included angle, to ensure accurate adjustment.

The Applicant wishes to emphasize a very important further advantage of this invention. For certain conditions, frequently treated in intensive care units, the instant infusion rate, and also the average infusion rate, have to be accurate and constant. For those conditions, very sophisticated and expensive infusion apparatuses, which are electronic and sometimes logic or computer controlled, are currently used. Those apparatuses are sometimes not available (for example in battle conditions or when a mass accident occurs) or electricity to drive them is not available, or trained personnel/operators are not available (for example in rural areas). The Applicant believes that the devices of this invention can advantageously be used under such circumstances to closely proximate the performance of the very sophisticated and expensive electronic devices. Furthermore, in many cases, the devices of this invention will be of sufficient accuracy and consistency to be used instead of the sophisticated and expensive electronic devices.

The Applicant wishes further to emphasize certain advantageous aspects of the invention even though they have at least partially been expressly mentioned above or have been alluded to.

The Applicant envisages providing devices of the invention in different capacities, e.g. devices having capacities of 0 to 5; 0 to 10; 0 to 15 ml per minute, and the like. Such devices may advantageously be pre-calibrated to the middle of the respective range, e.g. 2,5; 5 and 7,5 ml per minute in the examples above. In use, they can then be fine calibrated to an exact, required rate.

It is envisaged that the droplet inducer will be adapted to form droplets of a size or volume commensurate with the capacity of the device to facilitate monitoring the flow rate. Thus, a small capacity device will have a droplet inducer which forms small droplets, and the like. Each device will then have an indication of the number of droplets which make up a specific volume, for example 15 drops per ml.

It is to be appreciated that the capacity of the levelling means will always be at least as high, and generally somewhat higher, than the maximum flow rate of the measuring orifice.

It is an advantage that a prescription can be given for the exact dosage required with the confidence that the prescription will be adhered to accurately and constantly, i.e. without fluctuation.

Figure 4:
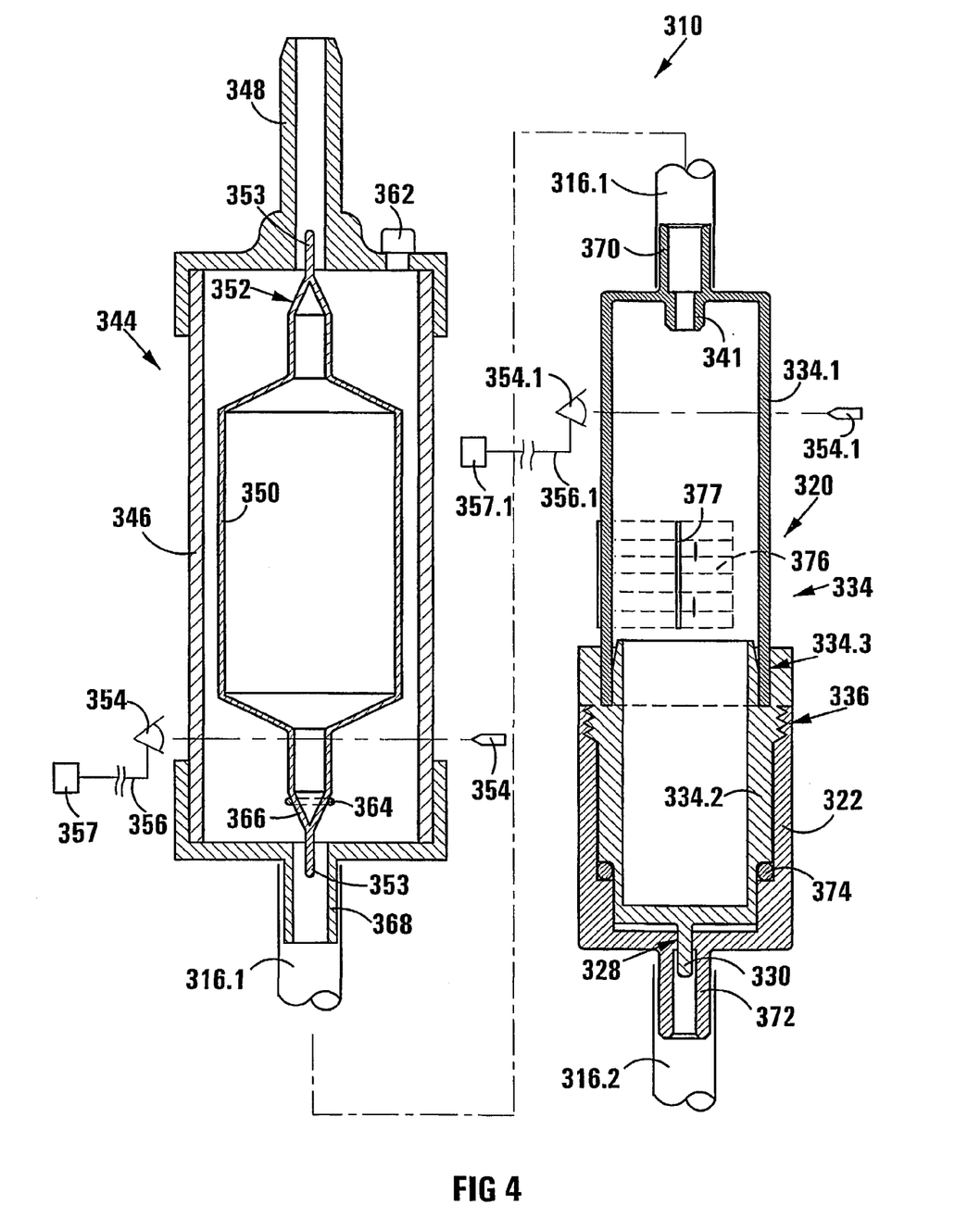

Yet a further embodiment of an infusion device in accordance with the invention is generally indicated by reference numeral 310 in FIG. 4. The device 310 of FIG. 4 is in principle the same as the devices in FIGS. 1 and 3, and like reference numerals are used to denote like features or components. Furthermore, the device 310 is not again described in detail, but emphasis is placed merely on changes.

In the pressure control device 344, taper closures 352, 366 close onto seats around respectively the inlet 348 and the outlet 368 of the housing 346. Whereas, in the embodiment of FIG. 3, a soft pliable material 264 is provided integral with the seat to enhance seating of the taper closure 366, in the embodiment of FIG. 4, the soft pliable material is integral with the closure 366 and the seat around the outlet 368 is of relatively harder material.

Furthermore, guiding pins 353 are provided co-axially with respectively the closure 352 at the upper end of the float 350 and the closure 366 at the lower end of the float 350. The pins 353 are substantially smaller than the inlet 348 and the outlet 368 and thus do not interfere with the flow. However, the pins 353 hold the closures in alignment with the inlet/outlet.

In the flow control device 320, the droplet inducer 341 is now integrally moulded with the inlet 370. The droplet inducer is in accordance with an appropriate standard, e.g. in the US in accordance with the FDA standard and in Europe in accordance with the EUP standard.

Furthermore, the upper housing 334 is in two sections, namely a top 334.1 and a bottom 334.2. The top is in the form of a resiliently flexible synthetic plastic moulding allowing it to act as a priming pump. A lower peripheral portion of the top 334.1 is snugly received in a circumferential slot 334.3 of the bottom 334. The taper needle 330 is integral with the lower section.

A sensor system 354.1, similar to the sensor systems 354 (FIG. 4) and 54 (FIG. 1) is provided in association with the droplet inducer 341 by means of which droplets dispensed can be counted. A signal line 356.1 leads to an electronic counter 357.1, which can be connected to an alarm system 357.1 to actuate an alarm when the droplet count moves outside of a predetermined range.

An 'O'-ring 364 forming a soft, pliable sealing surface, is located in a peripheral groove provided for that purpose on the taper closure 366 to seat on and seal with high integrity against the seat around the outlet 368.

What is claimed is:

1. A method of operating an infusion device infusing an infusing liquid into the human or animal body, the method including maintaining a constant level of said infusion liquid in a pressure control device which is in flow communication with, such as to be replenished from, a reservoir of said liquid, feeding said infusion under a constant liquid head commensurate with said constant level of said infusion liquid via a first flow line section, which is connected to a flow control device which is separate from and remote from and at a lower level to the pressure control device, dispensing by means of the flow control device the infusion liquid at a predetermined flow rate at a position correspondingly separate from, remote from and at a lower level to said constant level of said infusion liquid in said pressure control device, and conducting the infusion liquid at said predetermined flow rate, via a second flow line section to an infusion needle infusing said infusion liquid into the human or animal body.

2. A method of operating an infusion device as claimed in claim 1, including dripping the infusion liquid downstream of the pressure control device by means of a droplet inducer in a transparent chamber and counting the droplets against time to monitor the flow rate.

3. A method of operating an infusion device as claimed in claim 2 in which dripping said infusion liquid via the droplet inducer is upstream of the flow control device.

4. A method of operating an infusion device as claimed in claim 2 in which dripping said infusion liquid via the droplet inducer is downstream of the flow control device.

5. A method of operating an infusion device as claimed in claim 1 which includes rendering a section of the infusion device, which is subjected to said constant liquid head, downstream of the pressure control device sealed against atmosphere.

6. An infusion device as claimed in claim 5 in which the drip chamber has an inlet by means of which the flow control device is connected to the downstream end of the first flow line section,
the droplet inducer being arranged upstream of the orifice.

7. An infusion device as claimed in claim 5 which includes a sensor arranged to sense the droplets, and a counter responsive to said sensor to count droplets against time, and an alarm responsive to said counter to indicate an alarm condition when the droplet count falls outside of a predetermined range.

8. An infusion device for use in infusing an infusion liquid into the human or animal body, the infusion device including
a pressure control device including
a chamber,
an inlet into the chamber which inlet includes a connector for connecting the chamber in flow communication to a reservoir of infusion liquid,
an outlet from the chamber, and
a level control mechanism for controlling a level of said infusion liquid in the chamber at a constant level;
a flow control device including an orifice and an adjustable restrictor arranged, adjustably, to restrict flow through the orifice to a desired degree such as to dispense the infusion liquid at a selected flow rate;
a downstream or second flow line section connected at an upstream end thereof to the flow control device for receiving and conducting to an infusion needle the infusion liquid dispensed by the infusion device for infusion into the human or animal body;
in which said infusion device includes an upstream or first flow line section connected at an upstream end thereof to said chamber of the pressure control device, the first flow line section leading to the flow control device separate from, remote from, and at a relatively lower level to, the pressure control device, a downstream end of said first flow line section being connected to the flow control device.

9. An infusion device as claimed in claim 8 in which said pressure control device includes a vent hole at a high level through a wall of the chamber to subject said level of infusion liquid in the chamber to atmospheric pressure, in which said outlet from the chamber of the pressure control device is surrounded by a seat, in which said level control mechanism includes a float in said chamber and which is buoyant in said infusion liquid, an inlet closure connected to the float at an upper end thereof and being aligned with said inlet into the chamber to close the inlet when the level of infusion liquid in the chamber rises above a predetermined limit, an outlet closure connected to the float at a lower end thereof and aligned with said seat such as to close onto said seat to close the outlet against communication with the atmosphere via said vent hole when the level of infusion liquid in the chamber drops below a predetermined lower limit, one of said seat in the outlet and said outlet closure being of a material which is a silicone based polymer material and which is more pliable than the other of said seat in the outlet and said outlet closure, to enhance the integrity of sealing.

10. An infusion device as claimed in claim 9 which includes a sensor arranged to sense dropping of the float beyond a predetermined level, and an alarm responsive to said sensor to indicate an alarm condition.

11. An infusion device as claimed in claim 8 which includes a drip chamber downstream of and in flow communication with the pressure control device, and a droplet inducer arranged in the drip chamber to drip the infusion liquid being dispensed to allow the droplets to be counted.

12. An infusion device as claimed in claim 11 in which the droplet inducer is downstream of and below the orifice.

* * * * *